US012567493B2

(12) United States Patent
Lu et al.

(10) Patent No.: US 12,567,493 B2
(45) Date of Patent: Mar. 3, 2026

(54) SYSTEMS AND METHODS FOR DELAYED MEAL BOLUSES IN AUTOMATED INSULIN DELIVERY

(71) Applicant: Tandem Diabetes Care, Inc., San Diego, CA (US)

(72) Inventors: Virginia S. Lu, San Diego, CA (US); Nicholas Sherer, Escondido, CA (US); Thomas R Ulrich, Oceanside, CA (US); Katherine Vyvy Tran, San Diego, CA (US); Jose Ricardo Rueda, La Jolla, CA (US); Pat Mulvihill, San Diego, CA (US); Peter Zhao, San Diego, CA (US); Micah Stephens, San Diego, CA (US); Ryan Cardenas, San Diego, CA (US); Paul Harris, San Diego, CA (US); Geoffrey A. Kruse, San Diego, CA (US); Michael Michaud, San Diego, CA (US); Marissa Igartua, San Diego, CA (US)

(73) Assignee: TANDEM DIABETES CARE, INC., San Diego, CA (US)

( * ) Notice: Subject to any disclaimer, the term of this patent is extended or adjusted under 35 U.S.C. 154(b) by 765 days.

(21) Appl. No.: 17/964,513

(22) Filed: Oct. 12, 2022

(65) Prior Publication Data

US 2023/0113755 A1     Apr. 13, 2023

Related U.S. Application Data

(60) Provisional application No. 63/254,935, filed on Oct. 12, 2021.

(51) Int. Cl.
*G16H 20/17*          (2018.01)

(52) U.S. Cl.
CPC .................................. *G16H 20/17* (2018.01)

(58) Field of Classification Search
None
See application file for complete search history.

(56) References Cited

U.S. PATENT DOCUMENTS

| 3,833,030 A | 9/1974 | Waldbauer |
| 5,135,491 A | 8/1992 | Baldwin |

(Continued)

OTHER PUBLICATIONS

Notification of Transmittal of The International Search Report and The Written Opinion of the International Searching Authority, or The Declaration in PCT/US2022/046369 dated Feb. 20, 2023, 11 pages.

(Continued)

*Primary Examiner* — Manuel A Mendez
(74) *Attorney, Agent, or Firm* — Merchant & Gould P.C.

(57)          ABSTRACT

Disclosed herein are apparatuses and methods that can provide a delayed bolus calculator for use in closed loop diabetes therapy that can account for additional factors not taken into account in regular meal bolus calculations when a user wants to deliver a meal bolus a period of time after a meal was consumed. A delayed bolus calculator can enable the user to enter a period of time since the meal was consumed in addition to the number of carbohydrates consumed in a meal. This enables the system to account for the amount of increased insulin from the closed loop algorithm in response to the meal and/or the time since the meal to ensure that the risk of hypoglycemia is mitigated while still reducing hyperglycemia.

20 Claims, 12 Drawing Sheets

(56)                    References Cited

U.S. PATENT DOCUMENTS

| | | | |
|---|---|---|---|
| 5,182,258 | A | 1/1993 | Chiou |
| 5,278,142 | A | 1/1994 | Chiou |
| 5,295,967 | A | 3/1994 | Rondelet et al. |
| 5,338,157 | A | 8/1994 | Blomquist |
| 5,568,884 | A | 10/1996 | Bruna |
| 5,626,566 | A | 5/1997 | Petersen et al. |
| 5,858,393 | A | 1/1999 | Bymaster et al. |
| 5,885,614 | A | 3/1999 | Hirsch |
| 6,142,939 | A | 11/2000 | Eppstein et al. |
| 6,283,197 | B1 | 9/2001 | Kono |
| 6,309,371 | B1 | 10/2001 | Deboer et al. |
| 6,364,866 | B1 | 4/2002 | Dawe |
| 6,374,683 | B1 | 4/2002 | Hunicke-Smith et al. |
| 6,468,242 | B1 | 10/2002 | Wilson et al. |
| 6,485,463 | B1 | 11/2002 | Yeh |
| 6,537,268 | B1 | 3/2003 | Gibson et al. |
| 6,699,234 | B2 | 3/2004 | Yeh |
| 7,022,071 | B2 | 4/2006 | Schaupp |
| 7,118,351 | B2 | 10/2006 | Effenhauser et al. |
| 8,109,885 | B2 | 2/2012 | Heske et al. |
| 9,486,171 | B2 | 11/2016 | Saint |
| 9,486,571 | B2 | 11/2016 | Rosinko |
| 9,669,160 | B2 | 6/2017 | Harris et al. |
| 9,833,177 | B2 | 12/2017 | Blomquist |
| 9,867,937 | B2 | 1/2018 | Saint et al. |
| 9,867,953 | B2 | 1/2018 | Rosinko |
| 10,016,561 | B2 | 7/2018 | Saint et al. |
| 10,052,049 | B2 | 8/2018 | Blomquist et al. |
| 10,569,016 | B2 | 2/2020 | Rosinko |
| 10,726,100 | B2 | 7/2020 | Blomquist et al. |
| 10,943,687 | B2 | 3/2021 | Blomquist |
| 11,116,901 | B2 | 9/2021 | Harris |
| 11,217,339 | B2 | 1/2022 | Blomquist |
| 11,224,693 | B2 | 1/2022 | Ulrich et al. |
| 11,291,763 | B2 | 4/2022 | Blomquist et al. |
| 11,464,908 | B2 | 10/2022 | Michaud et al. |
| 11,471,598 | B2 * | 10/2022 | Estes .................... G16H 20/17 |
| 11,607,492 | B2 | 3/2023 | Rosinko et al. |
| 11,621,899 | B1 | 4/2023 | Bettaiah et al. |
| 11,654,236 | B2 | 5/2023 | Kearns et al. |
| 11,676,694 | B2 | 6/2023 | Kruse et al. |
| 11,738,130 | B2 | 8/2023 | Helmore et al. |
| 2002/0076679 | A1 | 6/2002 | Aman |
| 2003/0086583 | A1 | 5/2003 | Maltan et al. |
| 2003/0160683 | A1 | 8/2003 | Blomquist |
| 2003/0163088 | A1 | 8/2003 | Blomquist |
| 2004/0064097 | A1 | 4/2004 | Peterson |
| 2008/0171967 | A1 | 7/2008 | Blomquist et al. |
| 2009/0177142 | A1 | 7/2009 | Blomquist et al. |
| 2009/0177147 | A1 | 7/2009 | Blomquist et al. |
| 2010/0145276 | A1 | 6/2010 | Yodfat et al. |
| 2011/0133946 | A1 | 6/2011 | Kopp et al. |
| 2011/0196610 | A1 | 8/2011 | Waldman et al. |
| 2012/0245556 | A1 | 9/2012 | Kovatchev et al. |
| 2014/0285663 | A1 | 9/2014 | Schofield et al. |
| 2016/0342754 | A1 | 11/2016 | Vettoretti et al. |
| 2019/0074078 | A1 | 3/2019 | Booth et al. |
| 2020/0368430 | A1 | 11/2020 | Ulrich et al. |
| 2021/0001044 | A1 | 1/2021 | Michaud et al. |
| 2021/0113766 | A1 | 4/2021 | Kearns et al. |
| 2021/0154405 | A1 | 5/2021 | Kearns et al. |
| 2021/0353857 | A1 | 11/2021 | Ulrich et al. |
| 2022/0062553 | A1 | 3/2022 | Constantin et al. |
| 2022/0101978 | A1 | 3/2022 | Blomquist |
| 2022/0233772 | A1 | 7/2022 | Ulrich et al. |
| 2022/0233773 | A1 | 7/2022 | Rueda et al. |
| 2022/0265927 | A1 | 8/2022 | Harris et al. |
| 2023/0034408 | A1 | 2/2023 | Nichols et al. |
| 2023/0037465 | A1 | 2/2023 | Rueda et al. |
| 2023/0040677 | A1 | 2/2023 | Tran et al. |
| 2023/0230668 | A1 * | 7/2023 | Lee .................... A61M 5/1723 |
| | | | 604/66 |

OTHER PUBLICATIONS

Supplementary European Search Report for Application No. 22881689, PCT/US2022/046369, mailed Aug. 5, 2025, 9 pages.

* cited by examiner

500

Operate pump according to AID
algorithm     502

Delayed bolus calculator menu
item selected   504

Delayed bolus calculator
displayed   506

Carbs in meal and time since
meal entered   508

Calculate delayed meal bolus
510

Display delayed bolus amount
for confirmation     512

Deliver delayed bolus   514

SYSTEMS AND METHODS FOR DELAYED MEAL BOLUSES IN AUTOMATED INSULIN DELIVERY

RELATED APPLICATION

The present application claims the benefit of U.S. Provisional Application No. 63/254,935, filed Oct. 12, 2021, which is hereby incorporated herein in its entirety by reference.

TECHNICAL FIELD

The present disclosure relates generally to ambulatory infusion pumps and, more particularly, to operation of ambulatory infusion pumps in a closed-loop or semi-closed-loop fashion.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type 1, or in some cases, type 2 diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as blood glucose meters (BGMs) and continuous glucose monitoring devices (CGMs). A CGM provides a substantially continuous estimated blood glucose level through a transcutaneous sensor that estimates blood analyte levels, such as blood glucose levels, via the patient's interstitial fluid CGM systems typically consist of a transcutaneously-placed sensor, a transmitter and a monitor.

Ambulatory infusion pumps typically allow the patient or caregiver to adjust the amount of insulin or other medicament delivered, by a basal rate or a bolus, based on blood glucose data obtained by a BGM or a CGM, and in some cases include the capability to automatically adjust such medicament delivery. Some ambulatory infusion pumps may include the capability to interface with a BGM or CGM such as, e.g., by receiving measured or estimated blood glucose levels and automatically adjusting or prompting the user to adjust the level of medicament being administered or planned for administration or, in cases of abnormally low blood glucose readings, reducing or automatically temporarily ceasing or prompting the user temporarily to cease or reduce insulin administration. These portable pumps may incorporate a BGM or CGM within the hardware of the pump or may communicate with a dedicated BGM or CGM via wired or wireless data communication protocols, directly and/or via a device such as a smartphone. One example of integration of infusion pumps with CGM devices is described in U.S. Patent Publication No. 2014/0276419, which is hereby incorporated by reference herein.

As noted above, insulin or other medicament dosing by basal rate and/or bolus techniques could automatically be provided by a pump based on readings received into the pump from a CGM device that is, e.g., external to the portable insulin pump or integrated with the pump as a pump-CGM system in a closed-loop or semi-closed-loop fashion. With respect to insulin delivery, some systems including this feature can be referred to as artificial pancreas systems because the systems serve to mimic biological functions of the pancreas for patients with diabetes. Such systems are also referred to as automated insulin delivery (AID) systems.

Some AID systems primarily deliver medicament automatically based on CGM readings, but also enable users to program meal boluses. Consumption of carbohydrates in a meal causes blood glucose to rise, which can be counteracted by insulin or other medicament delivered in a meal bolus. If a user delays in delivering the meal bolus, the user's blood glucose may begin to rise prior to the meal bolus being delivered. This can be problematic with AID systems that automatically deliver correction boluses (and/or increase a basal rate) based on CGM readings, because the system may deliver a correction bolus in response to the CGM readings and the user then subsequently delivers a meal bolus. This "insulin stacking" resulting from two separate insulin deliveries intended to counteract the same rise in blood glucose can cause the user's blood glucose to drop to a low level.

SUMMARY

Disclosed herein are apparatuses and methods that can provide a delayed bolus calculator for use in closed loop diabetes therapy that can account for additional factors not taken into account in regular meal bolus calculations when a user wants to deliver a meal bolus a period of time after a meal was consumed. A delayed bolus calculator can enable the user to enter a period of time since the meal was consumed in addition to the number of carbohydrates consumed in a meal. This enables the system to account for the amount of increased insulin from the closed loop algorithm in response to the meal and/or the time since the meal to ensure that the risk of hypoglycemia is mitigated while still reducing hyperglycemia.

In an embodiment, a system for closed loop diabetes therapy can include a pump mechanism configured to facilitate delivery of insulin to a user, a communications device adapted to receive glucose levels from a continuous glucose monitor, a user interface and at least one processor functionally linked to the pump mechanism, the user interface and the communications device. The at least one processor can be configured to automatically calculate insulin doses for the user with a closed loop delivery algorithm based on glucose levels received from the continuous glucose monitor and to automatically deliver the calculated insulin doses to the user. If user input selecting a delayed bolus calculator menu item on the user interface is received, a delayed bolus calculator can be displayed on the user interface enabling a user to enter an amount of carbohydrates consumed in a meal and an amount of time that has passed since the meal was consumed. The at least one processor can then calculate a delayed bolus amount for the user accounting for the amount of carbohydrates consumed in the meal and any increased insulin delivered by the closed loop algorithm due to the meal over the time that has passed since the meal was consumed. The pump mechanism can then deliver the delayed bolus amount to the user.

In an embodiment, method for closed loop diabetes therapy can include automatically calculating insulin doses for a user with a closed loop delivery algorithm based on glucose levels received from a continuous glucose monitor and automatically delivering the calculated insulin doses to the user with a pump mechanism of an ambulatory infusion pump system. Upon receiving user input selecting a delayed bolus calculator menu item on a user interface of the ambulatory infusion pump system, a delayed bolus calculator can be displayed on the user interface. Entry of an amount of carbohydrates consumed in a meal and an amount of time that has passed since the meal was consumed can be received through the bolus calculator. A delayed bolus amount can then be calculated for the user accounting for the amount of carbohydrates consumed in the meal and any increased insulin delivered by the closed loop algorithm due to the meal over the time that has passed since the meal was consumed and delivered to the user.

In an embodiment, a system for closed loop diabetes therapy can include a pump mechanism configured to facilitate delivery of insulin to a user, a communications device adapted to receive glucose levels from a continuous glucose monitor, a user interface and at least one processor functionally linked to the pump mechanism, the user interface and the communications device. The at least one processor can be configured to automatically calculate insulin doses for the user with a closed loop delivery algorithm based on glucose levels received from the continuous glucose monitor and automatically deliver the calculated insulin doses to the user. User input programming a meal bolus for at a time after a meal was consumed can be received including a number of carbohydrates in the meal and an amount of time that has passed since the meal was consumed. A delayed bolus amount can be calculated for the user accounting for the amount of time that has passed since the meal was consumed and delivered to the user with the pump mechanism.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which.

Figure 1:
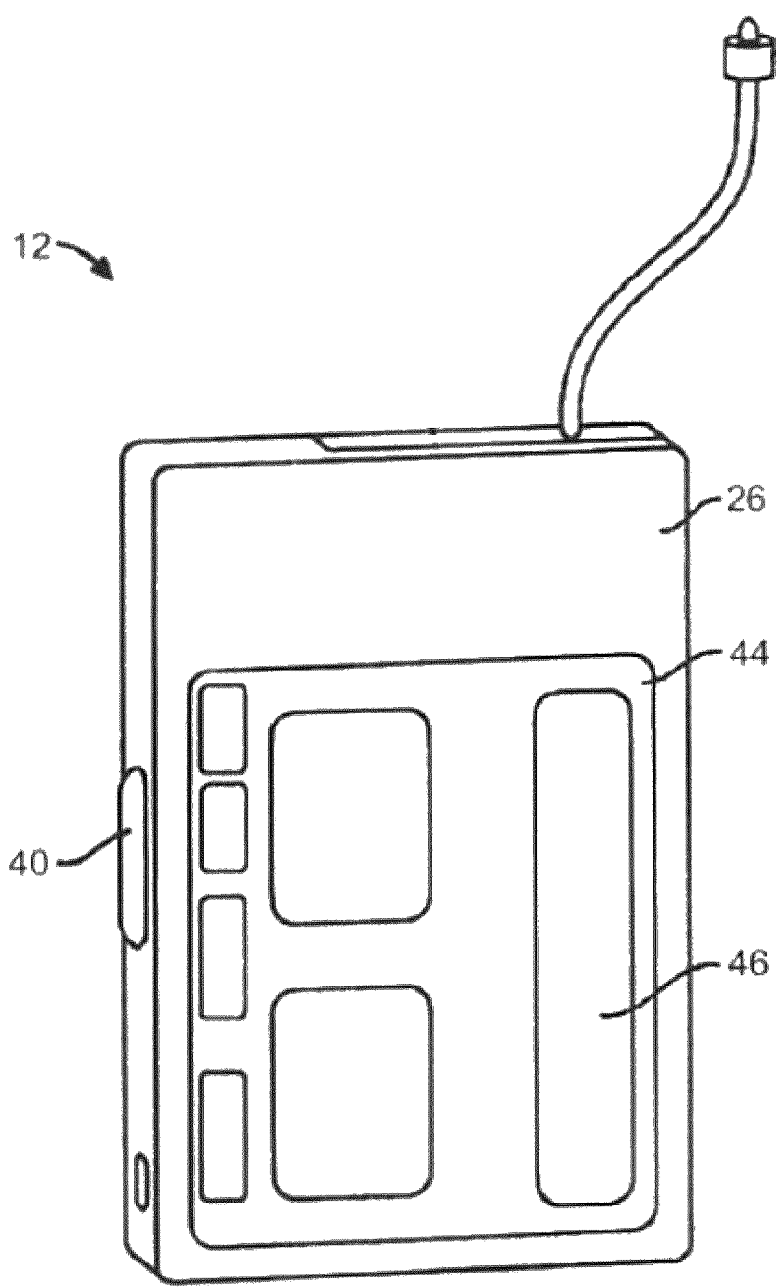
FIG. 1 is a medical device that can be used with embodiments of the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the disclosure.

FIG. 1 depicts an embodiment of a medical device according to the disclosure. In this embodiment, the medical device is configured as a pump 12. Pump 12 may be an infusion pump that includes a pumping or delivery mechanism and reservoir for delivering medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

In one embodiment, the medical device can be an ambulatory insulin pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient.

Figure 2:
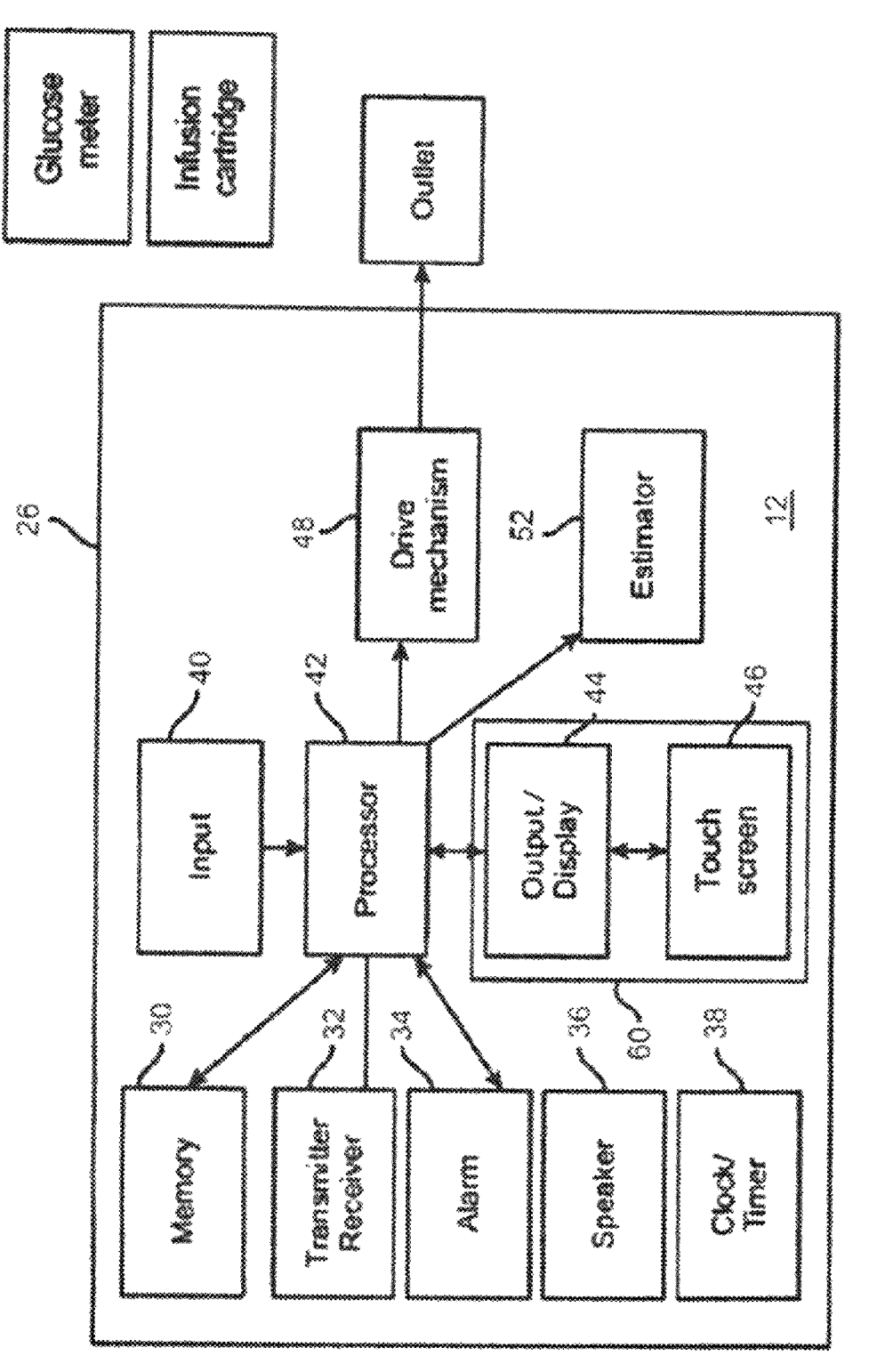
FIG. 2 is a block diagram representing a medical device that can be used with embodiments of the disclosure.

FIG. 2 illustrates a block diagram of some of the features that can be used with embodiments, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters.

Figures 3A, 3B:
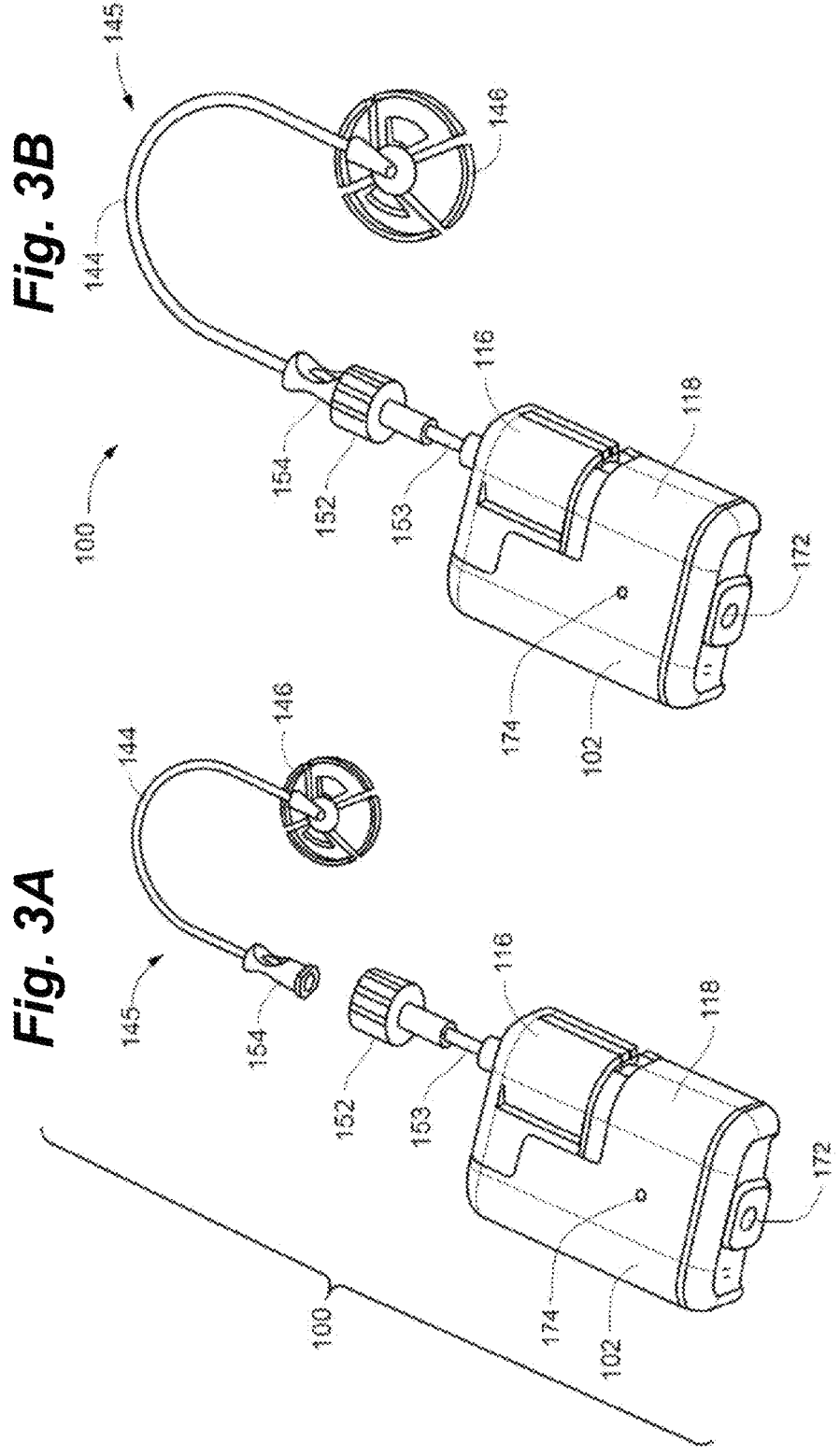
FIGS. 3A-3B depict an embodiment of a pump system according to the disclosure.

FIGS. 3A-3B depict another pump system including a pump 102 that can be used with embodiments. Drive unit 118 of pump 102 includes a drive mechanism 122 that mates with a recess in disposable cartridge 116 of pump 102 to attach the cartridge 116 to the drive unit 118. Pump system 100 can further include an infusion set 145 having a connector 154 that connects to a connector 152 attached to pump 102 with tubing 153. Tubing 144 extends to a site connector 146 that can attach or be pre-connected to a cannula and/or infusion needle that punctures the patient's skin at the infusion site to deliver medicament from the pump 102 to the patient via infusion set 145. In some embodiments, pump can include a user input button 172 and an indicator light 174 to provide feedback to the user.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. In one embodiment pump 102 does not include a display but may include one or more indicator lights 174 and/or one or more input buttons 172. Pump 102 can also incorporate any or all of the features described with respect to pump 12 in FIG. 2. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
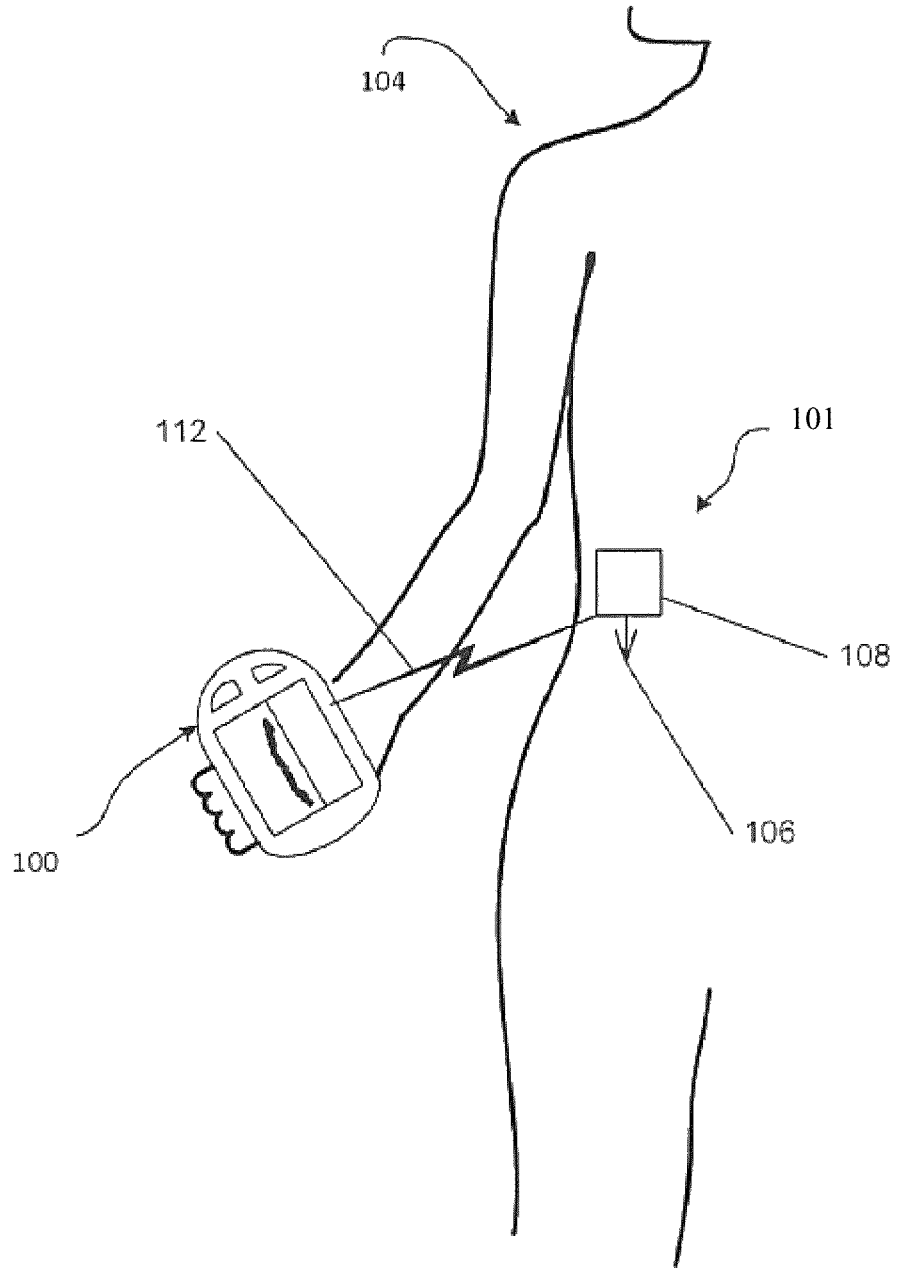
FIG. 4 is a schematic representation of a system according to the disclosure.

Pump 12 or 102 can interface directly or indirectly (via, e.g., a smartphone or other device) with a glucose meter, such as a blood glucose meter (BGM) or a continuous glucose monitor (CGM). Referring to FIG. 4, an exemplary CGM system 100 according to an embodiment of the present invention is shown (other CGM systems can be used). The illustrated CGM system includes a sensor 101 affixed to a patient 104 that can be associated with the insulin infusion device in a CGM-pump system. The sensor 101 includes a sensor probe 106 configured to be inserted to a point below the dermal layer (skin) of the patient 104. The sensor probe 106 is therefore exposed to the patient's interstitial fluid or plasma beneath the skin and reacts with that interstitial fluid to produce a signal that can be associated with the patient's blood glucose (BG) level. The sensor 101 includes a sensor body 108 that transmits data associated with the interstitial fluid to which the sensor probe 106 is exposed. The data may be transmitted from the sensor 101 to the glucose monitoring system receiver 100 via a wireless transmitter, such as a near field communication (NFC) radio frequency (RF) transmitter or a transmitter operating according to a "Wi-Fi" or Bluetooth® protocol, Bluetooth® low energy protocol or the like, or the data may be transmitted via a wire connector from the sensor 101 to the monitoring system 100. Transmission of sensor data to the glucose monitoring system receiver by wireless or wired connection is represented in FIG. 4 by the arrow line 112. Further detail regarding such systems and definitions of related terms can be found in, e.g., U.S. Pat. Nos. 8,311,749, 7,711,402 and 7,497,827, each of which is hereby incorporated by reference in its entirety.

In an embodiment of a pump-CGM system having a pump 12, 102 that communicates with a CGM and that integrates CGM data and pump data as described herein, the CGM can automatically transmit the glucose data to the pump. The pump can then automatically determine therapy parameters and deliver medicament based on the data. Such an automatic pump-CGM system for insulin delivery can be referred to as an automated insulin delivery (AID) or an artificial pancreas system that provides closed-loop therapy to the patient to approximate or even mimic the natural functions of a healthy pancreas. In such a system, insulin doses are calculated based on the CGM readings (that may or may not be automatically transmitted to the pump) and are automatically delivered to the patient at least in part based on the CGM reading(s). In various embodiments, doses can be delivered as automated correction boluses and/or automated increases or decreases to a basal rate. Insulin doses can also be administered based on current glucose levels and/or predicted future glucoses levels based on current and past glucose levels.

For example, if the CGM indicates that the user has a high blood glucose level or hyperglycemia, the system can automatically calculate an insulin dose necessary to reduce the user's blood glucose level below a threshold level or to a target level and automatically deliver the dose. Alternatively, the system can automatically suggest a change in therapy upon receiving the CGM data such as an increased insulin basal rate or delivery of a bolus, but can require the user to accept the suggested change prior to delivery rather than automatically delivering the therapy adjustments.

If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the user, e.g., ingest carbohydrates and/or take other actions and/or make other suggestions as may be appropriate to address the hypoglycemic condition, singly or in any desired combination or sequence. Such determination can be made by the infusion pump providing therapy or by a separate device that transmits therapy parameters to the infusion pump. In some embodiments, multiple medicaments can be employed in such a system as, for example, a first medicament, e.g., insulin, that lowers blood glucose levels and a second medicament, e.g., glucagon, that raises blood glucose levels.

As with other parameters related to therapy, such thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

Automated insulin delivery (AID) systems such as those described above can also enable a user to manually program meal boluses of insulin or other medicaments to counteract the rise in blood glucose caused by the consumption of carbohydrates. However, if the user is unable to program a meal bolus when the meal is consumed or forgets to program the bolus the user can be left with a difficult choice as to how to address the meal. If the user does not bolus, extended hyperglycemia can occur and time in range may be poor as the closed loop algorithm attempts to compensate for the rise in blood glucose from the carbohydrates by incrementally increasing insulin delivery each interval. If the user does program a bolus at the later time, there is a risk of hypoglycemia due to the "insulin stacking" that can occur if the AID system first delivers a correction bolus and/or increases a basal rate in response to the rise in blood glucose caused by the carbohydrates and the user then subsequently programs the meal bolus. While in theory the closed-loop algorithm can subtract increased insulin delivered in response to the consumption of the meal from the programmed meal bolus, the system cannot automatically determine whether the insulin increase was due to the meal or was delivered to correct a high or rising glucose level that occurred for reasons other than consumption of the meal. Embodiments disclosed herein therefore can include a delayed bolus calculator that can be presented to a user to inform the system of the previous meal and need for a delayed meal bolus.

In embodiments, a delayed bolus calculator can enable a user to enter the amount of time since the meal was consumed and use an adjusted meal bolus formula to account for automated insulin increases to avoid insulin stacking. Typically, a meal bolus is calculated with the formula $$Bolus = \frac{Carbs}{CR},$$

in which CR is the user's carbohydrate ratio, to provide an amount of insulin to compensate for the carbohydrates consumed in the meal. Some systems will further account for whether more or less insulin than the amount that compensates for the carbohydrates is needed due to the user's current glucose level, e.g., being low or high, by employing the formula $$Bolus = \frac{Carbs}{CR} + \left(\frac{BG - 110}{CF} - IOB\right),$$

in which 110 is an example target glucose level and IOB is the current amount of insulin on board in the user. However, such calculations can lead to over-delivery of insulin if delivery has been increased by the closed loop algorithm in response to rising glucose levels from a meal for which a meal bolus was delayed.

In embodiments, IOB can be calculated using Swan4 hr_IOB or Swan6 hr_IOB, which are known methods of estimating the amount of metabolically active insulin in the body. As is known in the art, the Swan IOB equation is IOB(t)=$\Sigma_{i=0}^{72}$(InsulinDelivered(i)−UserBasalRate)*Decay [i], in which i is an index for insulin delivery every five minutes for the past six hours and Decay is a decaying function of i that is different for Swan6 hr_IOB and Swan4 hrIob.

According to embodiments, a delayed bolus calculator as disclosed herein can account for two additional factors not taken into account in regular meal bolus calculations such as those set forth above. The first factor is the time since the user has eaten because blood glucose will eventually stop rising and begin falling due to basal insulin and non-insulin dependent pathways for glucose consumption even if no additional insulin is delivered along with a meal. For example, a user should not bolus a day after a meal was consumed to account for carbohydrates consumed yesterday. Although this example is an extreme circumstance, it illustrates that the body can otherwise begin compensating for the post-prandial rise in glucose without increased insulin. The second additional factor is any increased insulin automatically delivered by the closed loop algorithm in response to the increase in glucose levels caused by the meal to avoid insulin stacking.

In some embodiments, a delayed bolus calculation can account for only the second factor identified above, increased insulin from the closed loop algorithm, and not the first factor based on the time from when the meal was consumed. In such embodiments, the formula for calculation of a delayed meal bolus can be expressed as $$delayed\ bolus = \frac{Carbs}{CR} + min\left(\frac{BG - 110}{CF}, 0\right) - max(Swan6hr\_IOB, 0),$$

in which $$\frac{BG - 110}{CF}$$

is added to the bolus only if it is less than zero (i.e., the user's glucose level is below the, in this example, 110 mg/dL target which is unlikely following an un-bolused meal). The subtraction of the current IOB estimate taken at the time of the delayed bolus reduces insulin stacking by accounting for the extra insulin delivered since the meal was consumed.

As noted above, other embodiments for a delayed bolus calculation can account for both automated insulin delivery increases following the time of the meal and the time since the meal was consumed. One such embodiment that uses Swan6 hr_IOB to estimate insulin on board can use be expressed using the following formula:

Swan6*hrIOB* bolus =

$$\frac{Carbs}{CR} D_6(t) + min\left(\frac{BG - 110}{CF}, 0\right) - max(Swan6hr\_IOB, 0),$$

in which $D_6(t)$ accounts for the time since the meal was consumed because the rise in blood glucose due to a meal will begin to fall without additional insulin delivery and increased IOB as noted above. In one example, the values for various times can be based on the Swan6 hr_IOB decay curve as follows:

| t (delay)[min] | 15 | 30 | 45 | 60 | 75 |
|---|---|---|---|---|---|
| $D_6(t)$ | .9757 | .911 | .8284 | .688 | .6153 |

As with the previous embodiment, $$\frac{BG - 110}{CF}$$

is used in the calculation only if it is less than zero. Another embodiment can employ Swan4 hr_IOB that uses a faster decaying IOB and calculate a delayed bolus according to the following equation:

$Swan4hrIOB$ bolus =

$$\frac{Carbs}{CR} D_4(t) + \min\left(\frac{BG - 110}{CF}, 0\right) - \max(Swan4hr\_IOB, 0),$$

where $D_4(t)$ is based off of the Swan4 hr_IOB decay curve as follows:

| t (delay)[min] | 15 | 30 | 45 | 60 | 75 |
|---|---|---|---|---|---|
| $D_4(t)$ | .9312 | .7901 | .6355 | .4936 | .3739 |

The combination of subtracting IOB to account for extra insulin delivered due to the meal by the closed loop algorithm and with the Dn(t) coefficient accounting for the time since the meal was consumed together (or separately) help ensure that the risk of hypoglycemia is mitigated while still reducing hyperglycemia.

Figure 5:
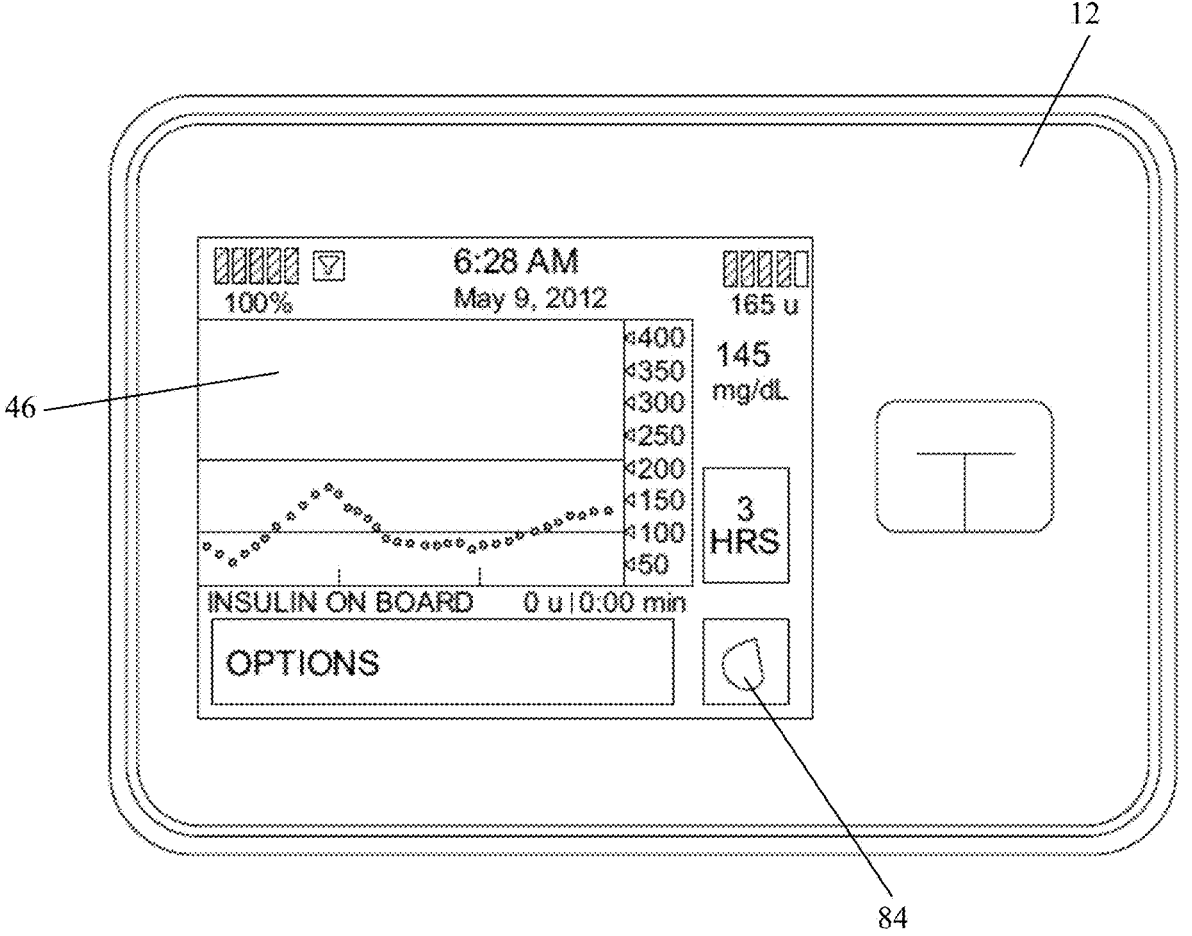
FIG. 5 is depicts a user interface for an ambulatory infusion pump system according to the disclosure.

In embodiments, a Delayed Bolus Calculator can be a user-selectable feature from a menu on a user's pump, remote control, smartphone, etc. For example, after a user selects a bolus object 84 on a user interface, such as a touchscreen 46 as depicted in FIG. 5, of a pump 12 or other device for controlling a pump, a Delayed Bolus Calculator page can be displayed. The Delayed Bolus Calculator can, in addition to enabling a user to enter a number of carbohydrates or units of insulin for the meal, enable the user to enter or select an amount of time since the meal was consumed. In one embodiment, a user can select from several predefined time increments, such as, for example, 15 minutes, 30 minutes, 45 minutes, 60 minutes and 75 minutes. The delayed bolus calculator can then use the amount of carbohydrates and the time since the meal in one of the formulas listed above to calculate a delayed bolus amount to account for the amount of increased insulin from the closed loop algorithm in response to the meal and/or the time since the meal. The calculated delayed bolus can then be presented to the user and delivered once confirmed by the user.

Figure 6:
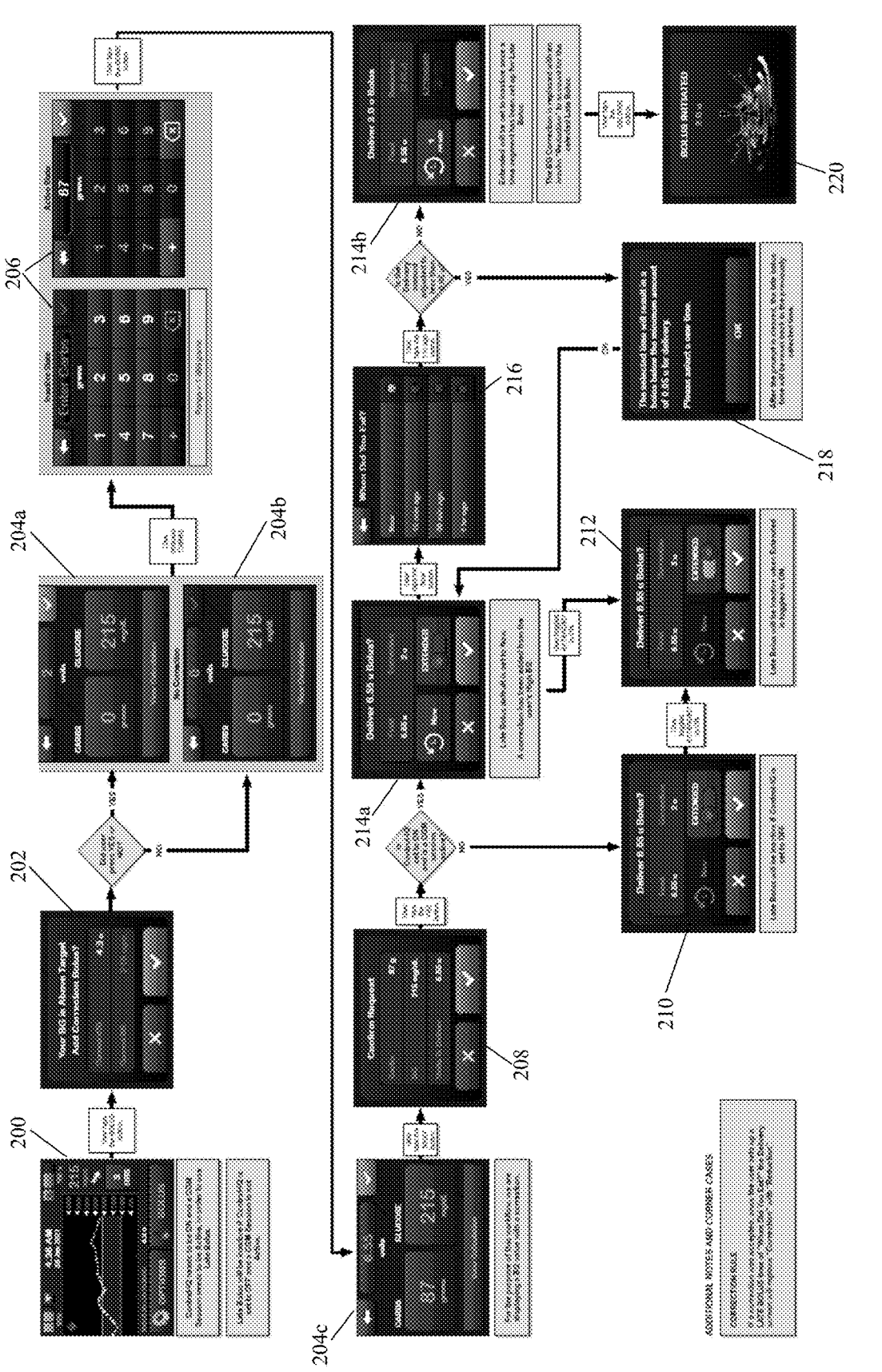
FIG. 6 depicts a series of menu screens that can be utilized by a user for delivery of a delayed bolus according to an embodiment.

One embodiment of a series of menu screens that can be presented on a touchscreen or other user interface for delivery of a delayed or late bolus according to an embodiment is depicted in FIG. 6. In this embodiment, in order for a delayed or late bolus to be programmed, the system must be operating according to a closed loop algorithm and there must be an active CGM session (i.e., the system is actively receiving CGM data). In the depicted example, the user's current and/or predicted future glucose level is above a target level so that upon selection of the bolus button on the homescreen 200, the user is prompted on a correction bolus screen 202 whether or not to include a correction bolus with the selected meal bolus. Depending on whether the user elects to include a correction bolus, one of two different bolus programming screens 204a (already including 2 units of insulin prior to entering carbohydrates) or 204b is depicted. From either screen 204a, 204b, the user will next select to enter the carbohydrates for the meal, which will cause a keypad entry screen 206 to be displayed to receive the user entry. Upon the user confirming the carbohydrate entry, the user interface can return to the bolus programming screen 204c, now displaying the entered number of carbohydrates and updated total bolus amount. Upon selecting the next icon, the user can be presented with a bolus confirmation screen 208. Once the user confirms the bolus, the system determines if the closed loop algorithm is operating and if a CGM session is active as noted above. If not, the system proceeds through delivery screens 210, 212 in which a late bolus is not available and cannot be selected on the screen. In some embodiments, late bolus is only available for delivery of an immediate bolus and not for delivery of an extended bolus (see transition between delivery screen 214a and delivery screen 212 deactivating the timing object 215 if extended bolus is selected).

Figures 6A, 6B, 6C:
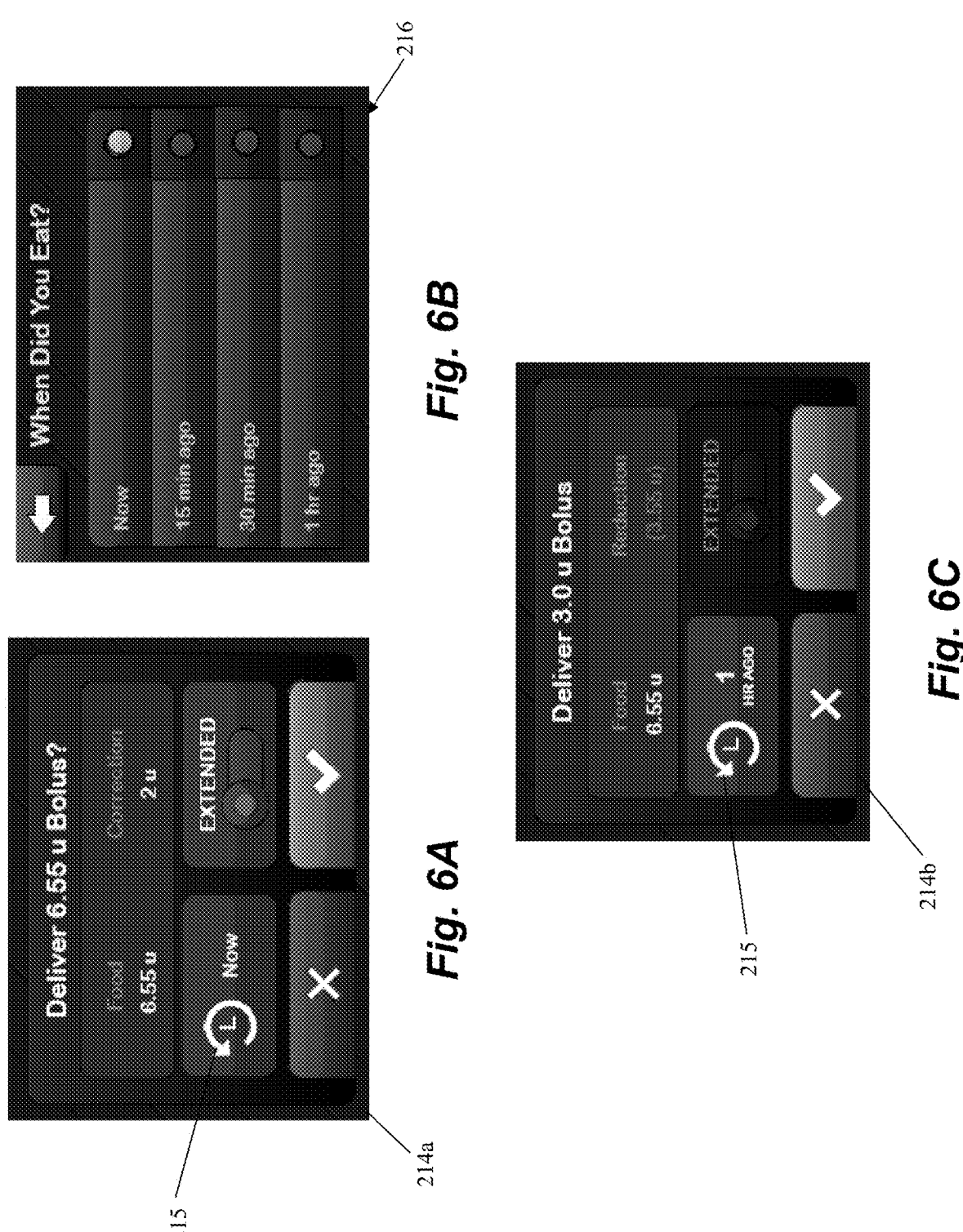
FIGS. 6A-6C depict various menu screens that can be utilized by a user for delivery of a delayed bolus according to an embodiment.

Still referring to FIG. 6, if the required conditions for a late bolus are active when the user confirms the bolus request on confirmation screen 208, the system displays a bolus delivery screen 214a that includes the ability to select a late bolus. Referring in more detail now to FIG. 6A, the bolus delivery screen can include a timing object 215. In some embodiments, the timing object is by default set to "Now" such that if the user is delivering a bolus for a current meal no additional input regarding timing of the meal is needed by the user to deliver the bolus. Selection of the timing object 215 can cause the system to display a "When Did You Eat?" screen 216 that can enable the user to select, in addition to "Now," various previous times when the user ate, such as, for example, 15 minutes, 30 minutes or 1 hour earlier. If the user selects a time other than "Now," the system can return to the delivery screen 214b. The timing object 215 will now reflect the timing selected by the user and the screen can display a "Reduction" calculated in one or more of the manners described above to account for the delay in delivering the bolus. In some embodiments, if the bolus amount is adjusted due to the delay to an amount under a minimum bolus delivery amount, such as, for example, 0.05 u, an error screen 218 can be displayed notifying the user that the bolus cannot be delivered and the user can then enter a different time or exit the bolus delivery calculator. Otherwise, once the user confirms the bolus in the bolus delivery screen 214b, a screen 220 indicating that the bolus has been initiated can be displayed.

Figure 7:
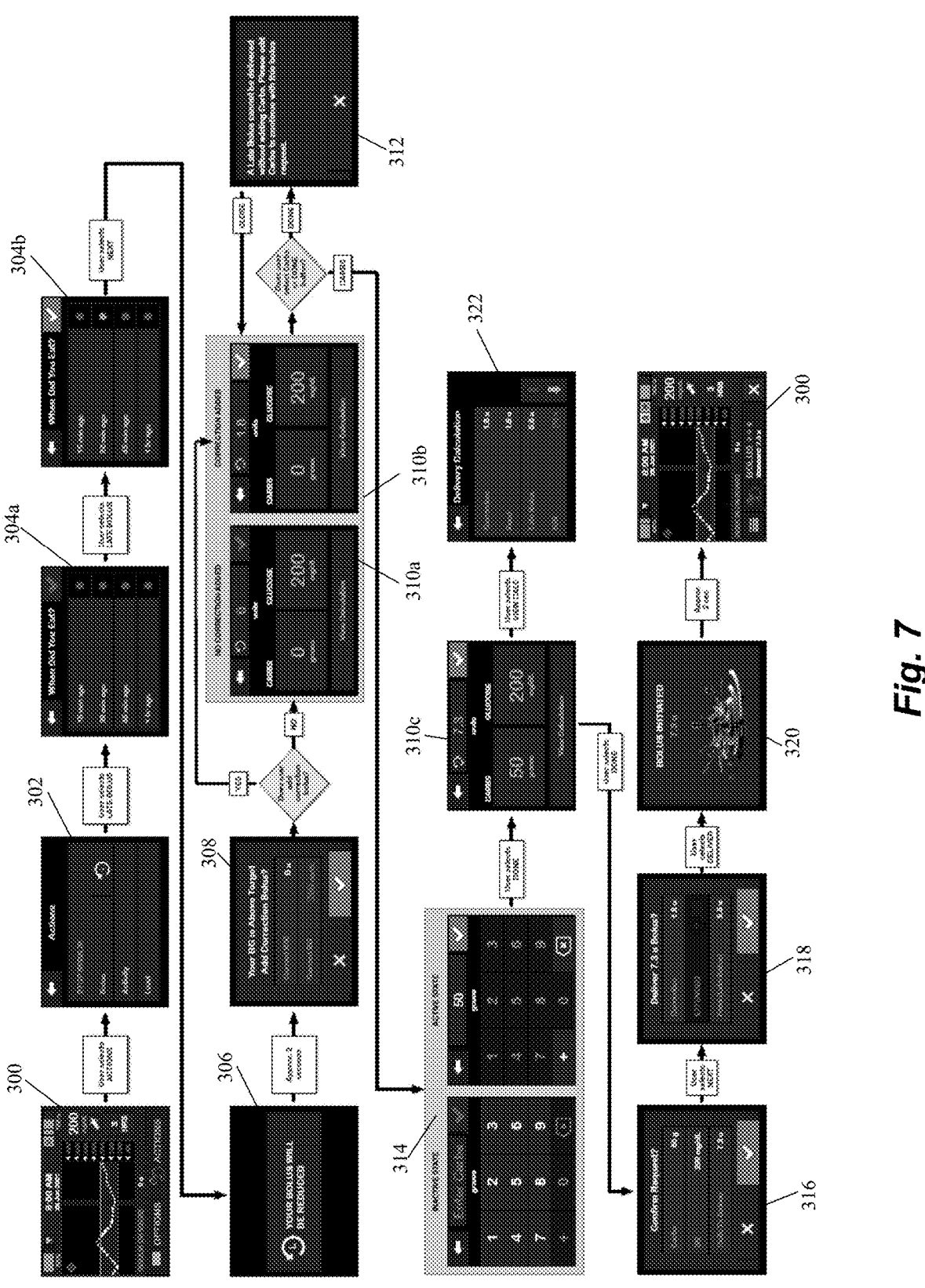
FIG. 7 depicts a series of menu screens that can be utilized by a user for delivery of a delayed bolus according to an embodiment.
Figures 7A, 7B, 7C:
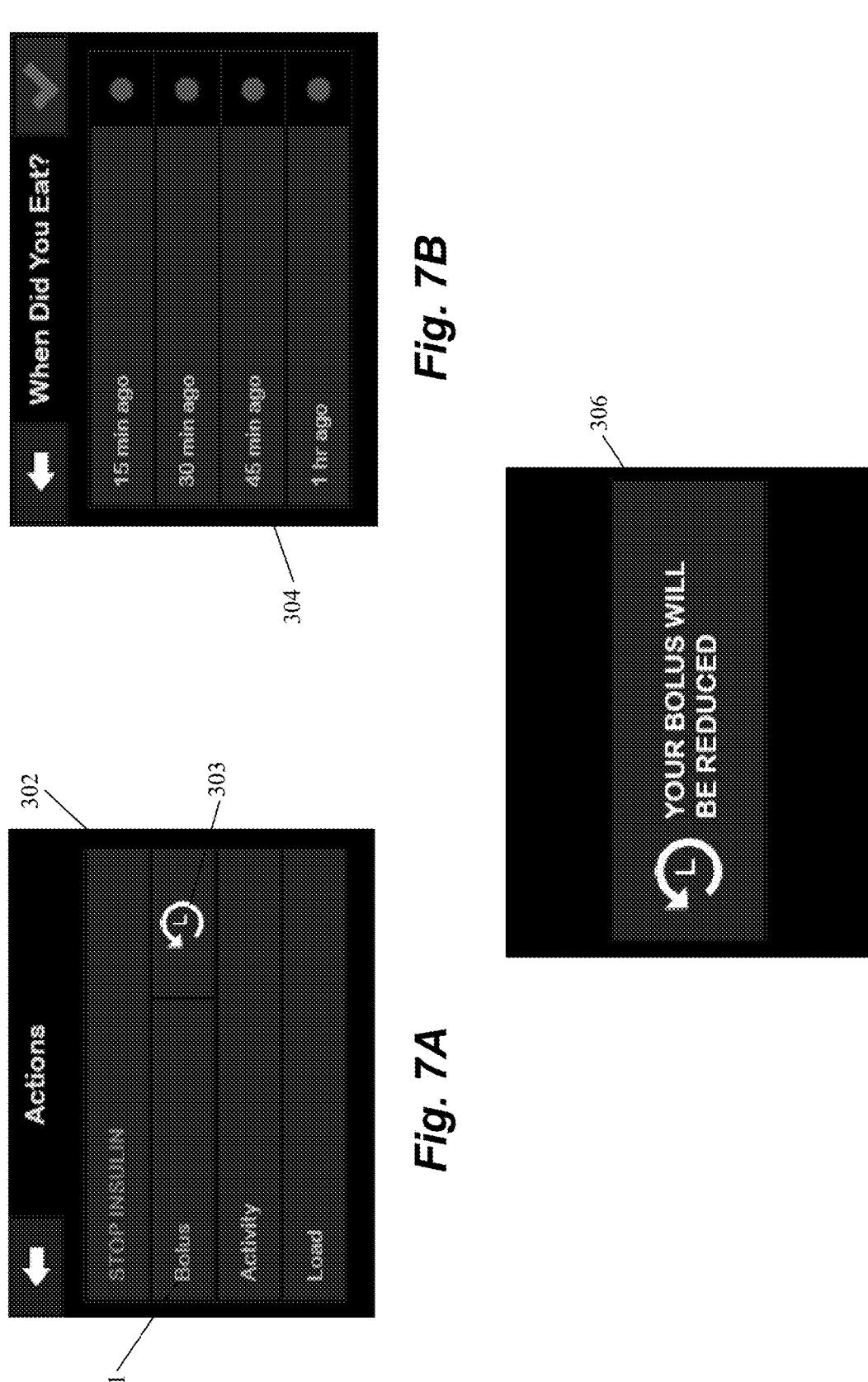
FIGS. 7A-7C depict various menu screens that can be utilized by a user for delivery of a delayed bolus according to an embodiment.

FIG. 7 depicts another embodiment of a series of menu screens that can be presented on a touchscreen or other user interface for delivery of a delayed or late bolus according to an embodiment. In this embodiment, the homescreen 300 includes an "Actions" object that upon being selected displays an Actions menu 302 that can include various menu items for, e.g., stopping insulin delivery, delivering a bolus, entering activity information/mode and loading or filling a cartridge. Referring in more detail to FIG. 7A, in an embodiment the user can select a Bolus object 301 in the Actions menu 302 to deliver a bolus for a current meal or can select a Late Bolus object 303 for delivery of a late bolus. If the user selects the Late Bolus object, the user can then select a time period as described above through a "When Did You Eat" screen 304a, 304b. Once the user confirms that the user will be programming a late bolus, a notification screen 306 informing the user that the bolus will be reduced can be displayed. The user then may optionally be brought through screens 308, 310a, 310b similar to those set forth above to add a correction bolus to the programmed bolus. If the user does not enter carbohydrates into the bolus calculation screen 310b, a notification screen 312 can be displayed to inform the user that a late bolus cannot be delivered without adding carbohydrates, whereas in bolus calculation screen 310a the user cannot navigate forward through the screen without entering carbohydrates. The user can then proceed through similar screens 314-320 and 310c for programming the bolus as those described above. A view calculation object can be selected in bolus calculation screen 310c to display details of the late bolus on Delivery Calculation screen 322.

Figure 8:
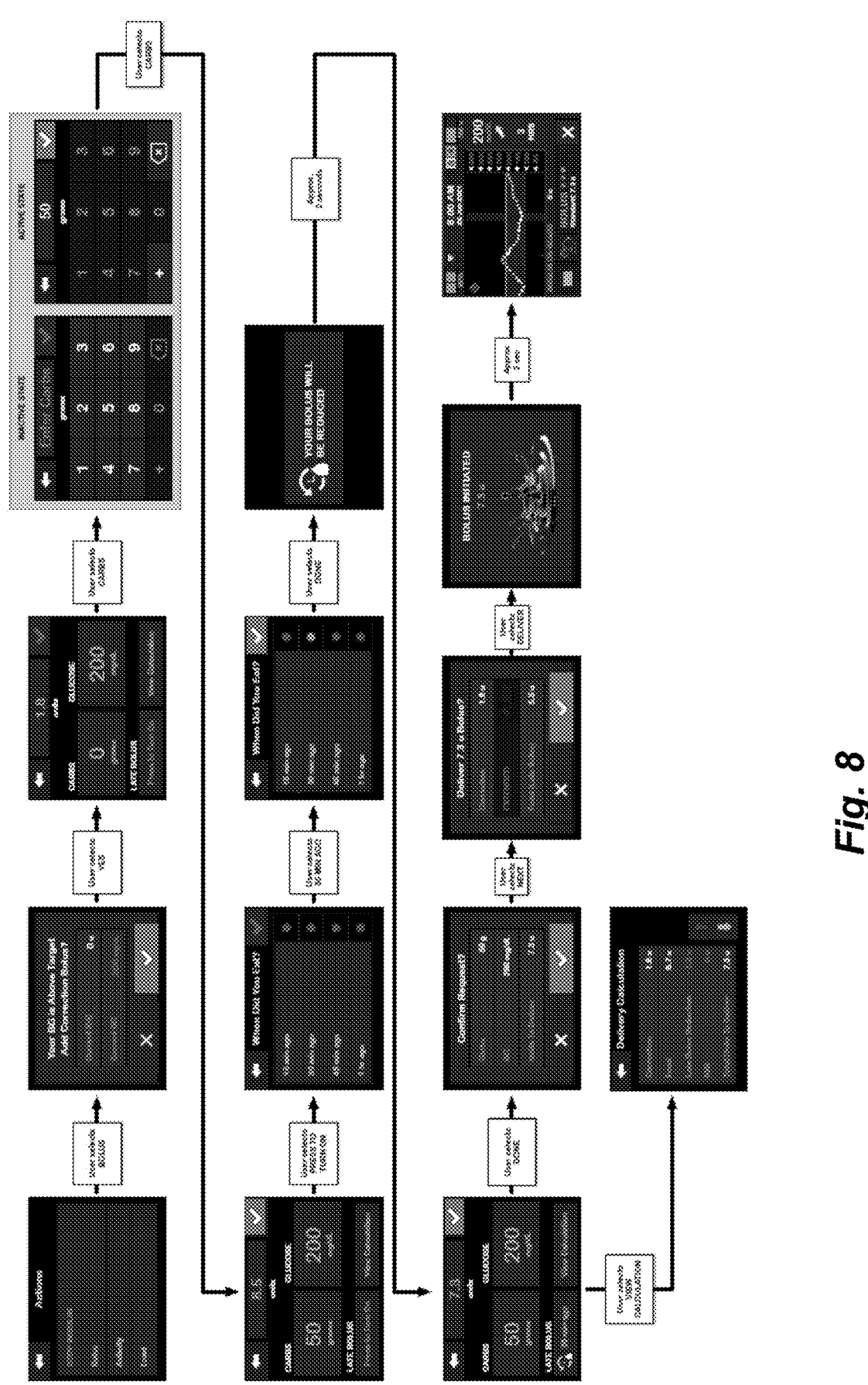
FIG. 8 depicts a series of menu screens that can be utilized by a user for delivery of a delayed bolus according to an embodiment.
Figure 8B:
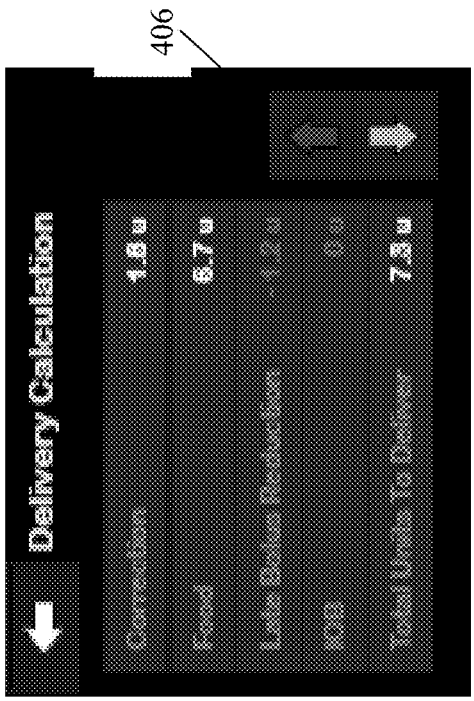
FIGS. 8A-8B depict various menu screens that can be utilized by a user for delivery of a delayed bolus according to an embodiment.
Figure 8A:
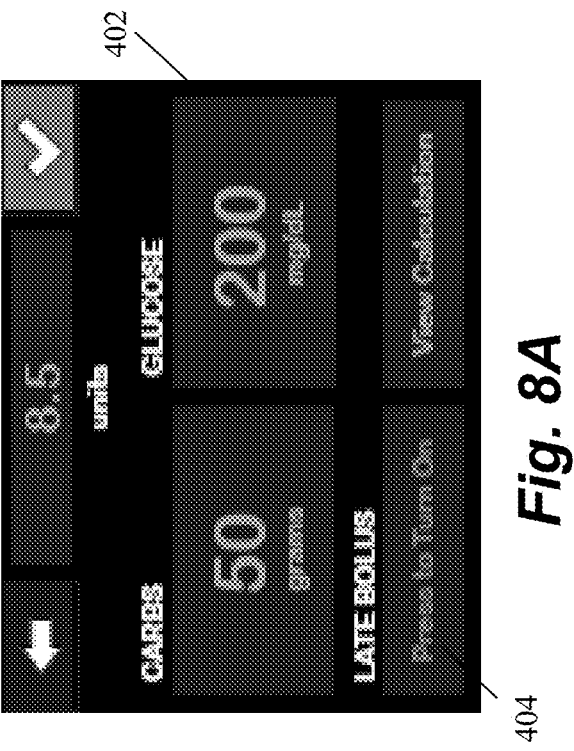

FIG. 8 depicts a similar embodiment of a series of menu screens to those described above that can be presented on a touchscreen or other user interface for delivery of a delayed or late bolus. In this embodiment, the bolus calculation screen 402 depicted in FIG. 8A includes a Late Bolus object 404 in the form of a "Press to Turn On" instruction to the user that enables the user to activate a Late Bolus feature by a touch selection of the Late Bolus object 404. Upon selecting the Late Bolus object 404 to "turn on" the feature, a When Did You Eat? Screen for programming the late bolus such as that previously described in FIG. 7B can be displayed and the user can be informed that the bolus will be reduced with a screen such as that shown in FIG. 7C. In this embodiment, if the user selects to View Calculation in the bolus calculation screen 402 after programming the late bolus, a Delivery Calculation screen 406 can be displayed as depicted in FIG. 8B that shows the amount by which the bolus was reduced.

Figure 9:
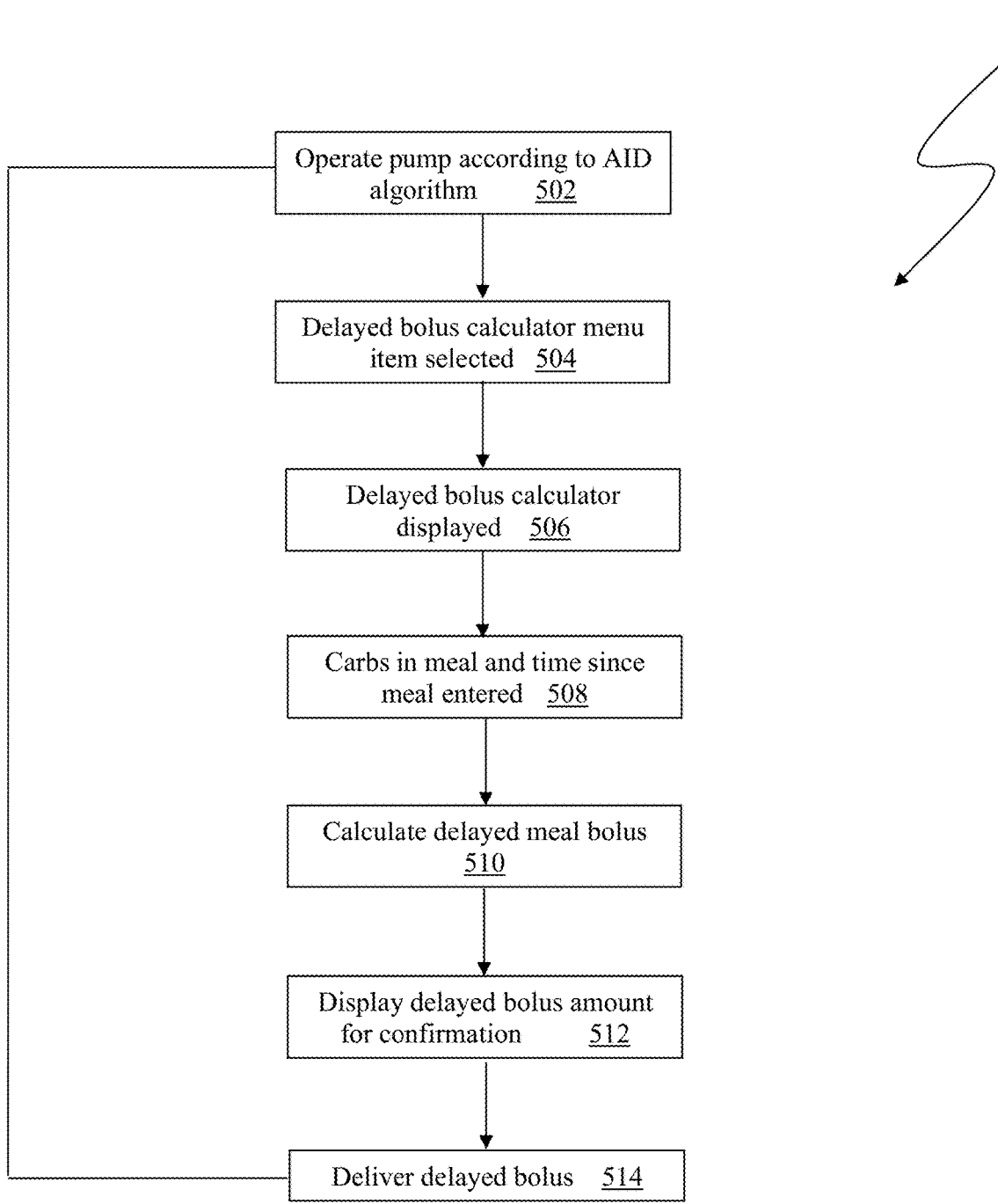
FIG. 9 is a flowchart of a method of delivering medicament in automated insulin delivery systems according to an embodiment.

Referring now to FIG. 9, a method 500 of delivering boluses in automated insulin delivery systems according to an embodiment is depicted. At step 402, the pump is being operated according to a closed loop algorithm to automatically calculate and deliver insulin to the user based on glucose levels received from the continuous glucose monitor. At step 404, a delayed bolus calculator menu item is selected on a user interface of the system and in response a delayed bolus calculator screen is displayed on the user interface at step 406. The number of carbohydrates in the meal and the time since the meal can then be entered into the system at step 408 using the delayed bolus calculator. At step 410, the system can then calculate a delayed meal bolus to account for the amount of increased insulin from the closed loop algorithm in response to the meal and/or the time since the meal as disclosed herein. The calculated delayed bolus can then be displayed to the user on the user interface for confirmation at step 412 and delivered to the user following confirmation at step 414. The system then returns to standard operation of the closed loop algorithm.

Significant simulations of patient therapy of both single meal scenarios and multiple meal and/or day scenarios using a delayed bolus calculator as described herein for delivery of meal boluses after a meal was consumed in conjunction with closed loop therapy showed improved glycemic outcomes by improving time in range and reducing hypoglycemia when bolusing after a meal.

Although the delayed bolus calculator features disclosed herein are primarily described with respect to a user selection of a delayed bolus calculator menu item to indicate to the system that a bolus for a previously consumed meal is desired, there are circumstances where in some embodiments such a delayed bolus calculator can be automatically displayed to the user. For example, alerts relating to high glucose levels such as glucose being over a high threshold, a rate of change of glucose increasing over a threshold and/or a future predicted glucose level being likely to be over a high threshold can cause the system to automatically display the delayed bolus calculator to provide the user with an opportunity to indicate to the system that the high alert was caused by an un-bolused meal and to deliver a delayed meal bolus to address the glucose levels resulting from the un-bolused meal. In addition, a missed meal bolus alarm that a user programs to remind the user to deliver a meal bolus during an expected meal time can also automatically cause the delayed bolus calculator to be displayed in case the user had consumed a meal during the expected meal time but had forgotten to bolus for the meal.

In embodiments, a system for closed loop diabetes therapy includes a pump mechanism configured to facilitate delivery of insulin to a user, a communications device adapted to receive glucose levels from a continuous glucose monitor, a user interface and at least one processor functionally linked to the pump mechanism, the user interface and the communications device. The at least one processor can be configured to automatically calculate insulin doses for the user with a closed loop delivery algorithm based on glucose levels received from the continuous glucose monitor and automatically deliver the calculated insulin doses to the user. User input can be received selecting a delayed bolus calculator menu item on the user interface and a delayed bolus calculator can be displayed on the user interface. The delayed bolus calculator can enable a user to enter an amount of carbohydrates consumed in a meal and an amount of time that has passed since the meal was consumed. A delayed bolus amount can be calculated for the user accounting for the amount of carbohydrates consumed in the meal and any increased insulin delivered by the closed loop algorithm over the time that has passed since the meal was consumed. The pump mechanism can then deliver the delayed bolus amount to the user.

In some embodiments, the at least one processor is configured to account for the amount of carbohydrates in the meal by calculating an initial bolus amount, the initial bolus amount calculated by dividing the amount of carbohydrate by a stored carbohydrate ratio of the user.

In some embodiments, wherein the at least one processor is further configured to estimate a current insulin on board for the user when the delayed bolus is programmed.

In some embodiments, the delayed bolus amount accounts for any increased insulin delivered by the closed loop algorithm due to the meal over the time that has passed since the meal was consumed by subtracting the estimated current insulin on board from the initial bolus amount.

In some embodiments, the at least one processor is further configured to modify the delayed bolus amount based on the amount of time that has passed since the meal was consumed.

In some embodiments, the at least one processor reduces the delayed bolus amount based on the amount of time that has passed since the meal was consumed.

In some embodiments, the at least one processor reduces the delayed bolus amount based on an insulin decay curve.

In some embodiments, the at least one processor is further configured to determine if the user's current glucose level is below a target glucose level when the delayed bolus amount is calculated.

In some embodiments, the at least one processor is further configured to reduce the delayed bolus amount if the user's current glucose level is below the target glucose level when the delayed bolus amount is calculated.

In embodiments, a system for closed loop diabetes therapy can include a pump mechanism configured to facilitate delivery of insulin to a user, a communications device adapted to receive glucose levels from a continuous glucose monitor, a user interface and at least one processor functionally linked to the pump mechanism, the user interface and the communications device. The at least one processor can be configured to automatically calculate insulin doses for the user with a closed loop delivery algorithm based on glucose levels received from the continuous glucose monitor and automatically deliver the calculated insulin doses to the user. User input programming a meal bolus for at a time after a meal was consumed can be received including a number of carbohydrates in the meal and an amount of time that has passed since the meal was consumed. A delayed bolus amount can be calculated for the user accounting for the amount of time that has passed since the meal was consumed and delivered to the user with the pump mechanism.

In some embodiments, the at least one processor is configured to calculate an initial bolus amount, the initial bolus amount calculated by dividing the amount of carbohydrates by a stored carbohydrate ratio of the user.

In some embodiments, the at least one processor is configured to account for the amount of time that has passed since the meal was consumed in calculating the delayed bolus amount by accounting for any increased insulin delivered by the closed loop algorithm over the time that has passed since the meal was consumed.

In some embodiments, the at least one processor is further configured to estimate a current insulin on board for the user when the delayed bolus is programmed, and the processor accounts for any increased insulin delivered by the closed loop algorithm over the time that has passed since the meal was consumed by subtracting the current insulin on board from the initial bolus amount.

In some embodiments, the at least one processor is further configured to modify the delayed bolus amount based on the amount of time that has passed since the meal was consumed by reducing the initial bolus amount based on the amount of time that has passed since the meal was consumed.

In some embodiments, the at least one processor reduces the initial bolus amount based on an insulin decay curve.

In some embodiments, the at least one processor is further configured to determine if the user's current glucose level is below a target glucose level when the delayed bolus amount is calculated.

In some embodiments, the at least one processor is further configured to reduce the delayed bolus amount if the user's current glucose level is below the target glucose level when the delayed bolus amount is calculated.

In some embodiments, the at least one processor is further configured to display a delayed bolus calculator on the user interface, and the user input is received through the delayed bolus calculator.

In some embodiments, the delayed bolus calculator enables the user to enter the amount of carbohydrates consumed in a meal and the amount of time that has passed since the meal was consumed.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357, 603; 10,357,606; 10,492,141; 10,541,987; 10,569,016; 10,736,037; 10,888,655; 10,994,077; 11,116,901; 11,224, 693; 11,291,763; 11,305,057; 11,458,246; and 11,464,908 and commonly owned U.S. Patent Publication Nos. 2009/ 0287180; 2012/0123230; 2013/0053816; 2014/0276423; 2014/0276569; 2014/0276570; 2018/0071454; 2019/ 0307952; 2020/0206420; 2020/0329433; 2020/0368430; 2020/0372995; 2021/0001044; 2021/0113766; 2021/ 0154405; 2021/0353857; 2022/0062553; 2022/0139522; 2022/0223250; 2022/0233772; 2022/0233773; 2022/ 0238201; and 2022/0265927 and commonly owned U.S.

patent application Ser. Nos. 17/368,968; 17/729,464; 17/732,208; 17/878,681; 17/879,959; 17/886,998 and 17/896,492.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A system for closed loop diabetes therapy, comprising:
a pump mechanism configured to facilitate delivery of insulin to a user;
a communications device adapted to receive glucose levels from a continuous glucose monitor;
a user interface;
at least one processor functionally linked to the pump mechanism, the user interface and the communications device, the at least one processor configured to:
automatically calculate insulin doses for the user with a closed loop delivery algorithm based on glucose levels received from the continuous glucose monitor;
automatically deliver the calculated insulin doses to the user;
enable a user to enter an amount of carbohydrates consumed in a meal and an amount of time that has passed since the meal was consumed;
calculate a delayed bolus amount for the user, the delayed bolus amount accounting for the amount of carbohydrates consumed in the meal and any increased insulin delivered by the closed loop algorithm over the time that has passed since the meal was consumed; and
cause the pump mechanism to deliver the delayed bolus amount to the user.

2. The system of claim 1, wherein the at least processor is configured to account for the amount of carbohydrates in the meal by calculating an initial bolus amount, the initial bolus amount calculated by dividing the amount of carbohydrate by a stored carbohydrate ratio of the user.

3. The system of claim 2, wherein the at least one processor is further configured to estimate a current insulin on board for the user when the delayed bolus amount is programmed.

4. The system of claim 3, wherein the delayed bolus amount accounts for any increased insulin delivered by the closed loop algorithm due to the meal over the time that has passed since the meal was consumed by subtracting the estimated current insulin on board from the initial bolus amount.

5. The system of claim 1, wherein the at least one processor is further configured to modify the delayed bolus amount based on the amount of time that has passed since the meal was consumed.

6. The system of claim 5, wherein the at least one processor reduces the delayed bolus amount based on the amount of time that has passed since the meal was consumed.

7. The system of claim 6, wherein the at least one processor reduces the delayed bolus amount based on an insulin decay curve.

8. The system of claim 1, wherein the at least one processor is further configured to determine if the user's current glucose level is below a target glucose level when the delayed bolus amount is calculated.

9. The system of claim 8, wherein the at least one processor is further configured to reduce the delayed bolus amount if the user's current glucose level is below the target glucose level when the delayed bolus amount is calculated.

10. The system of claim 1, wherein the at least one processor is further configured to display a delayed bolus calculator on the user interface that enables the user to enter the amount of carbohydrates consumed in the meal and the amount of time that has passed since the meal was consumed.

11. A system for closed loop diabetes therapy, comprising:
a pump mechanism configured to facilitate delivery of insulin to a user;
a communications device adapted to receive glucose levels from a continuous glucose monitor;
a user interface;
at least one processor functionally linked to the pump mechanism, the user interface and the communications device, the at least one processor configured to:
automatically calculate insulin doses for the user with a closed loop delivery algorithm based on glucose levels received from the continuous glucose monitor;
automatically deliver the calculated insulin doses to the user;
receive user input programming a meal bolus for a time after a meal was consumed, the user input including a number of carbohydrates in the meal and an amount of time that has passed since the meal was consumed;
calculate a delayed bolus amount for the user, the delayed bolus amount accounting for the amount of time that has passed since the meal was consumed; and
cause the pump mechanism to deliver the delayed bolus amount to the user.

12. The system of claim 11, wherein the at least one processor is configured to calculate an initial bolus amount, the initial bolus amount calculated by dividing the amount of carbohydrates by a stored carbohydrate ratio of the user.

13. The system of claim 12, wherein the at least one processor is configured to account for the amount of time that has passed since the meal was consumed in calculating the delayed bolus amount by accounting for any increased insulin delivered by the closed loop algorithm over the time that has passed since the meal was consumed.

14. The system of claim 13, wherein the at least one processor is further configured to estimate a current insulin on board for the user when the delayed bolus amount is programmed, and the processor accounts for any increased insulin delivered by the closed loop algorithm over the time that has passed since the meal was consumed by subtracting the current insulin on board from the initial bolus amount.

15. The system of claim 12, wherein the at least one processor is further configured to modify the delayed bolus amount based on the amount of time that has passed since the meal was consumed by reducing the initial bolus amount based on the amount of time that has passed since the meal was consumed.

16. The system of claim 15, wherein the at least one processor reduces the initial bolus amount based on an insulin decay curve.

17. The system of claim 11, wherein the at least one processor is further configured to determine if the user's current glucose level is below a target glucose level when the delayed bolus amount is calculated.

18. The system of claim 17, wherein the at least one processor is further configured to reduce the delayed bolus amount if the user's current glucose level is below the target glucose level when the delayed bolus amount is calculated.

19. The system of claim 11, wherein the at least one processor is further configured to display a delayed bolus calculator on the user interface, and the user input is received through the delayed bolus calculator.

20. The system of claim 19, wherein the delayed bolus calculator enables the user to enter the amount of carbohydrates consumed in a meal and the amount of time that has passed since the meal was consumed.

* * * * *